(12) United States Patent
Benn et al.

(10) Patent No.: US 10,159,854 B2
(45) Date of Patent: Dec. 25, 2018

(54) COMPOSITION FOR ALTERING THE COLOR OF KERATIN FIBERS

(71) Applicant: L'OREAL, Paris (FR)

(72) Inventors: Mark Benn, Union, NJ (US); Michael DeGeorge, Old Bridge, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/074,172

(22) Filed: Mar. 18, 2016

(65) Prior Publication Data

US 2017/0266104 A1 Sep. 21, 2017

(51) Int. Cl.
| | |
|---|---|
| *A61K 8/92* | (2006.01) |
| *A61K 8/23* | (2006.01) |
| *A61K 8/25* | (2006.01) |
| *A61K 8/41* | (2006.01) |
| *A61K 8/46* | (2006.01) |
| *A61K 8/73* | (2006.01) |
| *A61K 8/81* | (2006.01) |
| *A61Q 5/08* | (2006.01) |
| *A61K 8/31* | (2006.01) |
| *A61K 8/44* | (2006.01) |
| *A61K 8/22* | (2006.01) |

(52) U.S. Cl.
CPC .................. *A61Q 5/08* (2013.01); *A61K 8/22* (2013.01); *A61K 8/25* (2013.01); *A61K 8/31* (2013.01); *A61K 8/44* (2013.01); *A61K 8/732* (2013.01); *A61K 8/8111* (2013.01); *A61K 8/8147* (2013.01); *A61K 2800/882* (2013.01)

(58) Field of Classification Search
CPC . A61K 8/92; A61K 8/732; A61K 8/25; A61K 8/23; A61K 8/8147; A61K 8/41; A61K 8/817; A61K 8/463; A61K 2800/882; A61K 2800/88; A61Q 5/08
USPC .................. 424/70.11, 70.12, 70.16
See application file for complete search history.

(56) References Cited

U.S. PATENT DOCUMENTS

| | | | |
|---|---|---|---|
| 7,470,725 B2 | 12/2008 | Schwertfeger et al. | |
| 8,021,651 B2 | 9/2011 | Hentrich et al. | |
| 9,114,088 B2 | 8/2015 | Konno et al. | |
| 2004/0226110 A1* | 11/2004 | Legrand | A61K 8/22 8/405 |
| 2005/0192366 A1 | 9/2005 | Ou et al. | |
| 2013/0042883 A1* | 2/2013 | DeGeorge | A61K 8/22 132/208 |

FOREIGN PATENT DOCUMENTS

| | | |
|---|---|---|
| CN | 105380817 A | 3/2016 |
| WO | 2007/051511 A1 | 5/2007 |
| WO | 2007/126410 A2 | 11/2007 |
| WO | 2011/139433 A2 | 11/2011 |
| WO | 2015/149975 A1 | 10/2015 |
| WO | 2017/021511 A1 | 2/2017 |

OTHER PUBLICATIONS

Brunauer et al., "Adsorption of Gases in Multimolecular Layers," Journal of the American Chemical Society, vol. 60, Feb. 1938, pp. 309-319.
International Search Report and Written Opinion for PCT/US2017/022642, dated Jun. 5, 2017.
Notification Concerning Transmittal of International Preliminary Report on Patentability for counterpart Application No. PCT/US2017/022642, dated Sep. 27, 2018.

* cited by examiner

*Primary Examiner* — Lezah Roberts
(74) *Attorney, Agent, or Firm* — The Marbury Law Group, PLLC

(57) ABSTRACT

Disclosed herein are compositions and methods for altering the color of hair comprising a first mixture comprising from about 1% to about 50% of at least one starch, from about 1% to about 50% of at least one liquid fatty substance and from about 0.5% to about 40% of at least one silica material, and a second mixture comprising from about 1% to about 40% of at least one oxidizing agent, from about 0.5% to about 30% of at least one acrylic polymer and from about 0.1% to about 10% of at least one chelant compound.

22 Claims, 2 Drawing Sheets

Lift Studies at Natural Level 3

Lift Studies at Natural Level 6

COMPOSITION FOR ALTERING THE COLOR OF KERATIN FIBERS

FIELD OF THE INVENTION

The disclosure relates to compositions for use on keratinous substances. In particular, it relates to a two-part system and methods for altering the color of hair.

BACKGROUND

Consumers desire to use cosmetic and personal care compositions that enhance the appearance of keratin fibers, such as hair, by changing the color of the hair and/or by imparting various properties to hair, for example, shine and conditioning. The process of changing the color of hair can involve depositing a color onto the hair, which provides a different shade or color to the hair, and/or lifting the color of the hair.

Lightening or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

In general, hair lightening or color lifting compositions may include the presence of oil-based raw materials such as hydrogenated polydecene, usually at low concentrations around 2%. While it may be beneficial for a hair lightening or color lifting composition to comprise a higher concentration of oil, adding high concentrations of oil will result in a clumpy and moist product that is not free flowing and not in powder form.

Thus, in order to reduce or avoid the drawbacks above, as well as to improve the cosmetic performance of hair lightening or color lifting compositions, the use of new and additional ingredients and novel combinations of ingredients are continuously sought. However, the choice of ingredients or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It is therefore desirable to provide the consumer with compositions and methods that can lift the color of hair and optionally deposit color onto hair in an efficient or improved manner, while preventing excess damage to the hair and/or providing other cosmetic advantages such as shine, conditioning, and a healthy appearance to the hair.

The disclosed embodiments provide a composition in the form of a powder with high concentrations of oil and method for altering the color of hair.

It has now been surprisingly and unexpectedly discovered that combining a free-flowing powdered oil mixture with an oxidizing mixture creates a hair color-altering composition that is then mixed with an oil-rich developer, for example, Chromatics 20V Developer, to produce a 2-part bleach system. The developer can, in various embodiments, be added before application to the hair. The powdered oil mixture comprises from about 1% to about 50% of at least one starch, from about 1% to about 50% of at least one liquid fatty substance, and from about 0.5% to about 40% of at least one silica material. The oxidizing mixture comprises from about 1% to about 40% of at least one oxidizing agent, from about 0.5% to about 30% of at least one acrylic polymer, and from about 0.1% to about 10% of at least one chelant compound.

A conventional 3-part bleach system comprises bleach powder, a booster, and the oil-rich developer. A 2-part bleach system described herein is easier and more convenient to mix and combine than a 3-part bleach system because there are only two parts to the system, the hair color-altering composition and the oil-rich developer. In a 3-part bleach system, any oil present in the system is due to the oil-rich developer. The 2-part bleach system has a high concentration of oil because oil is present in both the hair color-altering composition and the oil-rich developer. This high concentration of oil has been found, at least in certain embodiments, to increase the degree of lift and improve the overall appearance of the hair.

SUMMARY

The disclosure relates, in various embodiments, to a hair color-altering composition comprising a first mixture comprising from about 1% to about 50% of at least one starch, from about 1% to about 50% of at least one liquid fatty substance, and from about 0.5% to about 40% of at least one silica material, and a second mixture comprising from about 1% to about 40% of at least one oxidizing agent, from about 0.5% to about 30% of at least one acrylic polymer, and from about 0.1% to about 10% of at least one chelant compound. All weights above are relative to the total weight of the hair color-altering composition.

In further embodiments, the at least one starch is chosen from starches derived from corn, potato, sweet potato, pea, barley, wheat, rice, oat, sago, tapioca and sorghum; hydrolyzed starches chosen from dextrin and maltodextrin; modified starches; or mixtures thereof. In other embodiments, the at least one starch is chosen from corn starch, potato starch, dextrin, maltodextrin, or mixtures thereof.

In further embodiments, the at least one liquid fatty substance is chosen from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof. In other embodiments, the at least one liquid fatty substance is a mineral oil.

In further embodiments, the at least one silica material comprises silica particles chosen from hydrated silica, hydrophobic silica aerogel particle, or mixtures thereof.

In further embodiments, the at least one oxidizing agent is chosen from peroxides, persulfates, perborates, percarbonates, alkali metal bromates, ferricyanides, peroxygenated salts, or mixtures thereof. In other embodiments, the at least one oxidizing agent is chosen from persulfate and monopersulfate.

In further embodiments, the acrylic polymer is a cross-linked acrylic polymer. In other embodiments, the cross-linked acrylic polymer is selected from sodium polyacrylate, carbomer, acrylates C10-30 alkyl acrylate crosspolymer, or mixtures thereof.

In further embodiments, the chelant compound is selected from ethylenediaminetetraacetic acid (EDTA) and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; N-2-hydroxyethyliminodiacetic acid and its salts; ethyleneglycol-bis(beta-amino ethyl ether)-N,N-tetraacetic acid, pentasodium aminotrimethylene phosphonate, or mixtures thereof.

In further embodiments, the composition further comprises from about 0.1% to about 30% of at least one wax, at least one surfactant selected from anionic surfactants, nonionic surfactants, amphoteric surfactants or mixtures thereof, or at least one ingredient chosen from organic amines, carbonate compounds, emulsifying agents, fillers, pigments, conditioning agents, moisturizing agents, additional viscosity or thickening agents, shine agents, sequestering agents, fragrances, preservatives, pH modifiers/neutralizing agents, stabilizers, or mixtures thereof.

Additionally, there are embodiments wherein the pH of the composition ranges from about 8.5 to about 10.

The disclosed embodiments also relate to a method of altering the color of hair, the method comprising the steps of mixing the first mixture, the second mixture and an oil rich-developer, and applying the resulting composition to the hair for a sufficient period of time to achieve a desired level of lift of the color of the hair.

The disclosed embodiments also relate to a multi-compartment kit for altering the color of hair, comprising a first compartment comprising the above-described first mixture, and a second compartment comprising the above-described second mixture.

Additional features and advantages of the disclosed embodiments as claimed will be set forth in the detailed description which follows, and in part will be readily apparent to those skilled in the art from that description or recognized by practicing the invention as claimed herein, including the detailed description which follows, the claims, as well as the appended drawings.

It is to be understood that both the foregoing general description and the following detailed description present various embodiments of the disclosure, and are intended to provide an overview or framework for understanding the nature and character of the claims. The accompanying drawings are included to provide a further understanding of the disclosure, and are incorporated into and constitute a part of this specification. The drawings illustrate various embodiments of the disclosure and together with the description serve to explain the principles and operations of the disclosure.

BRIEF DESCRIPTION OF THE DRAWINGS

The accompanying drawings, which are included to provide a further understanding of the invention and are incorporated in and constitute a part of this specification, together with the description serve to explain the principles of the invention.

DETAILED DESCRIPTION OF THE INVENTION

Figure 1:
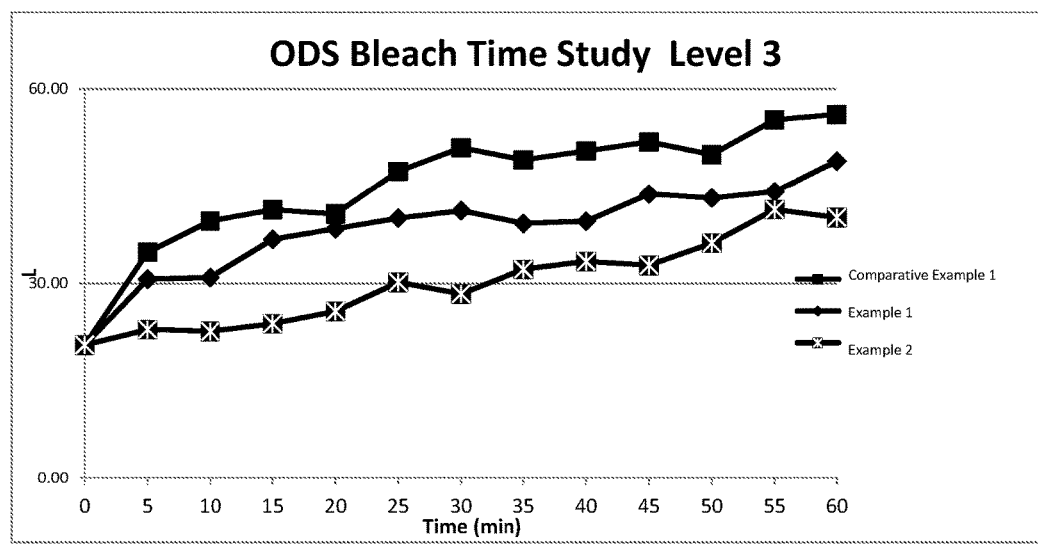
FIG. 1 is a graphical representation of lift studies for various hair color-altering systems, according to the exemplary embodiments of the disclosure.

It has been surprisingly and unexpectedly discovered that when a first mixture comprised of from about 1% to about 50% of at least one starch, from about 1% to about 50% of at least one liquid fatty substance, and from about 0.5% to about 40% of at least one silica material, is combined with a second mixture, comprised of from about 1% to about 40% of at least one oxidizing agent, from about 0.5% to about 30% of at least one acrylic polymer, and from about 0.1% to about 10% of at least one chelant compound, the resulting hair color-altering composition can be mixed with an oil-rich developer to produce a hair color-altering system with a high concentration of oil. The resulting hair color-altering system is easier to mix and combine. Additionally, the hair color-altering system increases the degree of lift and improves the overall appearance of the hair.

Starch

The compositions according to the disclosed embodiments comprise at least one starch.

The starch used may be chosen from macromolecules in the form of polymers formed from elemental units that are anhydroglucose units. The relative proportions of amylose and of amylopectin, and their degree of polymerization, vary as a function of the plant origin of the starches.

The starch may originate, for example, from a plant source such as cereals, tubers, roots, legumes and fruit. Thus, the starch may originate, for example, from a plant source chosen from corn, pea, potato, sweet potato, banana, barley, wheat, rice, oat, sago, tapioca and sorghum.

In some embodiments, the starch is in the form of a white powder, which is insoluble in cold water, and whose elemental particle size ranges from about 3 to about 100 microns. The starch used in the composition may be chemically modified via any suitable chemical reaction, including but not limited to pregelatinization, oxidation, crosslinking, and esterification.

Pregelatinization includes splitting the starch granules, for example by drying or cooking in a drying drum.

Oxidation may be carried out using strong oxidizing agents, which can lead to the introduction of carboxyl groups into the starch molecule and to depolymerization of the starch molecule. For example, a starch may be oxidized by treating an aqueous starch solution with sodium hypochlorite.

Crosslinking may be achieved using functional agents capable of reacting with the hydroxyl groups of the starch molecules, which will thus bond together different starch chains or different parts of the same starch chain with, for example, glyceryl and/or phosphate groups. Monostarch phosphates of the type Am-O—PO—(OX)2, distarch phosphates of the type Am-O—PO—(OX)—O-Am or tristarch phosphates of the type Am-O—PO—(O-Am)2 or mixtures thereof, Am meaning starch, may be obtained by crosslinking with phosphorus compounds. X may denote alkali metals, for example sodium or potassium, alkaline-earth metals, for example calcium or magnesium, ammonium salts, amine salts, for example those of monoethanolamine, diethanolamine, triethanolamine, or 3-amino-1,2-propanediol, or ammonium salts derived from basic amino acids such as lysine, arginine, sarcosine, ornithine, or citrulline.

The salts may be of alkali metals or alkaline-earth metals such as Na, $K_{1/2}$, Li, $NH_4$, or salts of a quaternary ammonium or of an organic amine such as monoethanolamine, diethanolamine or triethanolamine.

The phosphorus compounds may be, for example, sodium tripolyphosphate, sodium orthophosphate, phosphorus oxychloride or sodium trimetaphosphate. Starch phosphates may be, for example, hydroxypropyl starch phosphates, or compounds rich in starch phosphate.

Esterification may be carried out in an alkaline medium for the grafting of functional groups, for example, C1-C6 acyl (acetyl), d-C6 hydroxyalkyl (hydroxyethyl or hydroxypropyl), carboxy alkyl, octenylsuccinic, or sodium carboxymethyl.

When the starch is chemically modified via an esterification reaction, a carboxyalkyl starch is obtained. The carboxyalkyl starch may be, for example, a carboxy($C_1$-$C_4$) alkyl starch or a carboxymethyl starch.

Carboxyalkyl starches may be obtained by grafting carboxyalkyl groups onto at least one alcohol function of starch, for example, by reacting starch and sodium monochloroacetate in an alkaline medium.

In some embodiments, the carboxyalkyl groups may be attached via an ether function. In certain embodiments, the carboxyalkyl group is attached to carbon 1.

The degree of substitution preferably ranges from about 0.1 to about 1 or from about 0.15 to about 0.5. The degree of substitution is defined as the mean number of hydroxyl groups substituted with an ester or ether group, per monosaccharide unit of the polysaccharide.

In other embodiments, the starch may be chosen from amphoteric starches containing at least one anionic group and at least one cationic group. The anionic and cationic groups may be linked to the same reactive site of the starch molecule or to different reactive sites. The anionic groups may be of carboxylic, phosphate or sulfate type. The cationic groups may be of primary, secondary, tertiary or quaternary amine type.

In other embodiments, the starch may be chosen from hydrolyzed starches, for example, dextrins and maltodextrins.

Maltrodextrins and dextrins may be characterized with a Dextrose equivalent (DE). The DE is the number of grams of reducing sugars (considered as dextrose) per 100 g of product dry matter. The DE thus measures the degree of hydrolysis of the starch, as starches with higher DE comprise more small molecules such as dextrose and maltose, while starches with lower DE comprise large molecules such as polysaccharides. The DE of dextrins ranges from about 1 to about 13, and the DE of maltodextrins ranges from about 3 to about 20. In some embodiments, the starch may be chosen from corn starch, potato starch, dextrin, maltodextrin, or mixtures thereof. In other embodiments, the starch may be chosen from corn starch, maltodextrin, or mixtures thereof. A corn starch is available from the company Roquette under the tradename Amidon de Mais B. A maltodextrin is available from the company Grain Processing Corporation under the tradename Maltrin® M100.

In some embodiments, the starch for use in the composition is corn starch.

In other embodiments, the starch for use in the composition is maltodextrin. The starch is present in an amount ranging from about 1% to about 50% by weight, from about 2% to about 45% by weight, from about 3% to about 35% by weight, from about 4% to about 30% by weight, or from about 5% to about 25% by weight, relative to the total weight of the composition.

In certain embodiments, he starch is present in an amount ranging from about 1% to about 50% by weight, from about 2% to about 45% by weight, from about 3% to about 35% by weight, from about 4% to about 30% by weight, or from about 5% to about 25% by weight, relative to the total weight of the first mixture.

Liquid Fatty Substances

The compositions according to the disclosed embodiments comprise at least one liquid fatty substance, i.e. a compound that is liquid at a temperature of 25 degrees centigrade and at atmospheric pressure. A liquid fatty substance may also be referred to herein as an oil.

The term "fatty substance" means an organic compound that is insoluble in water at ordinary temperature, 25 degrees C., and at atmospheric pressure, 760 mmHg. The organic compound has a solubility of less than about 5 percent, less than about 1 percent, or less than about 0.1 percent. The fatty substance exhibits, in its structure, at least one hydrocarbon chain comprising at least 6 carbon atoms or a sequence of at least two siloxane groups. In some embodiments, the fatty substance may be soluble in organic solvents under ordinary temperature and atmospheric pressure conditions, for example, chloroform, dichloromethane, carbon tetrachloride, ethanol, benzene, toluene, tetrahydrofuran (THF), liquid petroleum jelly, decamethylcyclopentasiloxane, or mixtures thereof. The fatty substance does not contain any salified or unsalified carboxylic acid groups, for example, COOH or COO—.

The term "non-silicone o/V" means an oil not containing any silicon atoms and the term "silicone o/V" means an oil containing at least one silicon atom.

In certain embodiments, the liquid fatty substance may be chosen from $C_6$-$C_{16}$ hydrocarbons or hydrocarbons containing more than 16 carbon atoms, wherein the hydrocarbons are linear or branched hydrocarbons of mineral or synthetic origin having more than 16 carbon atoms. In other embodiments, the liquid fatty substance may be chosen from non-silicone oils of animal origin, plant oils of triglyceride type, synthetic triglycerides, fluoro oils, liquid fatty alcohols, liquid fatty acid and/or liquid fatty alcohol esters other than triglycerides and plant waxes, silicones oils, or mixtures thereof.

In certain embodiments, the fatty alcohols, esters and acids have at least one linear or branched, saturated or unsaturated hydrocarbon-based group comprising 6 to 30 or 8 to 30 carbon atoms. In other embodiments, the hydrocarbon-based group may be optionally substituted with at least one hydroxyl group or 1 to 4 hydroxyl groups. If they are unsaturated, these compounds may comprise 1 to 3 conjugated or unconjugated carbon-carbon double bonds.

In certain embodiments, the $C_6$-$C_{16}$ hydrocarbons may be linear, branched or cyclic. In other embodiments, the $C_6$-$C_{16}$ hydrocarbons may be alkanes, for example, hexane, dodecane, and isoparaffins such as isohexadecane, isododecane, and isodecane.

In certain embodiments, the non-silicone oil of animal origin may be perhydrosqualene.

In certain embodiments, the triglyceride oils of plant or synthetic origin may be chosen from liquid fatty acid triglycerides containing from 6 to 30 carbon atoms, for example, heptanoic or octanoic acid triglycerides, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the tradenames Miglyol® 810, 812 and 818 by the company Dynamit Nobel, jojoba oil, shea butter oil, or mixtures thereof.

In certain embodiments, the linear or branched hydrocarbons of mineral or synthetic origin having more than 16 carbon atoms may be chosen from liquid paraffins, petroleum jelly, liquid petroleum jelly, polydecenes or hydrogenated polyisobutene, such as Parleam®. In other embodiments, the fluoro oils may be chosen from perfluoromethylcyclopentane and perfluoro-1,3-dimethylcyclohexane, sold under the tradenames Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the tradenames PF 5050® and PF 5060® by the company 3M, or bromoperfluorooctyl sold under the tradename Foralkyl® by the company Atochem; nonafluoromethoxybutane and nonafluoroethoxyisobutane; or perfluoromorpholine derivatives such as 4-trifluoromethyl perfluoromorpholine sold under the tradename PF 5052® by the company 3M.

In certain embodiments, the liquid fatty alcohol may be chosen from saturated or unsaturated, linear or branched alcohols comprising from 6 to 30 carbon atoms, or from 8 to 30 carbon atoms, for example, octyldodecanol, 2-butyloctanol, 2-hexyldecanol, 2-undecylpentadecanol, oleyl alcohol or linoleyl alcohol.

In other embodiments, the liquid fatty acid may be chosen from saturated or unsaturated carboxylic acids comprising from 6 to 30 carbon atoms or from 9 to 30 carbon atoms, oleic acid, linoleic acid, linolenic acid, or isostearic acid. These acids may or may not be in the form of salts, i.e. if present, the composition may or may not contain organic or mineral alkaline agents such as sodium hydroxide, potassium hydroxide, monoethanolamine, or triethanolamine.

In certain embodiments, the liquid ester of a fatty acid and/or of fatty alcohol, which may be different from the triglycerides mentioned previously, may be chosen from liquid esters of saturated or unsaturated, linear or branched $C_1$-$C_{26}$ aliphatic monoacids or polyacids, or of saturated or unsaturated, linear or branched $C_1$-$C_{26}$ aliphatic monoalcohols or polyalcohols, the total carbon number of the esters being greater than or equal to 6 or greater than or equal to 10.

In other embodiments, the monoester may be chosen from isocetyl stearate; isodecyl neopentanoate; isostearyl neopentanoate; 2-ethylhexyl isononanoate; ethyl and isopropyl palmitates; alkyl myristates such as isopropyl myristate or ethyl myristate; or mixtures thereof.

In other embodiments, the ester may be of $C_4$-$C_{22}$ dicarboxylic or tricarboxylic acids and of $C_1$-$C_{22}$ alcohols, or of mono-, di- or tricarboxylic acids and of $C_2$-$C_{26}$ di-, tri-, tetra- or pentahydroxy alcohols.

In certain embodiments, the ester may be chosen from diethyl sebacate, diisopropyl sebacate, diisopropyl adipate, di-n-propyl adipate, dioctyl adipate, diisostearyl adipate, dioctyl maleate, glyceryl undecylenate, octyldodecyl stearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate, propylene glycol dicaprate, tridecyl erucate; triisopropyl citrate, triisostearyl citrate, glyceryl trilactate, glyceryl trioctanoate, trioctyldodecyl citrate, trioleyl citrate, propylene glycol dioctanoate, neopentyl glycol diheptanoate, diethylene glycol diisononanoate, or polyethylene glycol distearates.

In certain embodiments, the ester may be chosen from ethyl, isopropyl, myristyl, cetyl, or stearyl palmitate; 2-ethylhexyl palmitate; 2-octyldecyl palmitate; alkyl myristates such as isopropyl, butyl, cetyl, or 2-octyldodecyl myristate; hexyl stearate; butyl stearate; isobutyl stearate; dioctyl malate; hexyl laurate; 2-hexyldecyl laurate; isononyl isononanoate; cetyl octanoate; or mixtures thereof.

In certain embodiments, the composition may also comprise, as liquid fatty ester, sugar esters and diesters of $C_6$-$C_{30}$ or $C_{12}$-$C_{22}$ fatty acids. The term "sugar" means oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

In certain embodiments, the sugars may be chosen from sucrose or saccharose, glucose, galactose, ribose, fucose, maltose, fructose, mannose, arabinose, xylose, lactose, derivatives thereof, or alkyl derivatives thereof, for example methyl derivatives such as methylglucose.

In other embodiments, the sugar esters of fatty acids may be chosen from the group comprising the esters or mixtures of esters of sugars described previously and of linear or branched, saturated or unsaturated $C_6$-$C_{30}$ or $C_{12}$-$C_{22}$ fatty acids. If they are unsaturated, these compounds may comprise one to three conjugated or unconjugated carbon-carbon double bonds.

In other embodiments, the ester may be chosen from mono-, di-, tri- and tetraesters, polyesters, or mixtures thereof.

In other embodiments, the ester may be chosen from oleates, laurates, palmitates, myristates, behenates, cocoates, stearates, linoleates, linolenates, caprates, arachidonates, or mixtures thereof, for example, oleate/palmitate, oleate/stearate, or palmitate/stearate mixed esters.

In certain embodiments, the ester may be made of monoesters and diesters, such as mono- or di-oleate, -stearate, -behenate, -oleate/palmitate, -linoleate, -linolenate, or -oleate/stearate of sucrose, of glucose, or of methylglucose. An example is a methylglucose dioleate sold under the tradename Glucate® DO by the company Amerchol.

In certain embodiments, the silicone oil may be chosen from volatile or non-volatile, cyclic, linear, or branched silicones, which are unmodified or modified with organic groups, having a viscosity ranging from about $5\times10^{-6}$ to about 2.5 m²/s at 25 degrees centigrade, or about $1\times10^{-5}$ to 1 m²/s.

In certain embodiments, the silicone may be chosen from liquid polydialkylsiloxanes, for example, polydimethylsiloxanes (PDMS), or liquid organomodified polysiloxanes comprising at least one functional group chosen from amino groups and alkoxy groups.

Organopolysiloxanes are defined in greater detail in Walter Noll's Chemistry and Technology of Silicones (1968), Academic Press. They may be volatile or nonvolatile.

Volatile silicones may be chosen from those having a boiling point ranging from about 60 degrees centigrade to about 260 degrees centigrade, from cyclic polydialkylsiloxanes containing from 3 to 7 or from 4 to 5 silicon atoms, or from linear volatile polydialkylsiloxanes containing 2 to 9 silicon atoms and having a viscosity of less than or equal to $5\times10^{-6}$ m²/s at 25 degrees centigrade.

Examples of cyclic polydialkylsiloxanes containing from 3 to 7 or from 4 to 5 silicon atoms include octamethylcyclotetrasiloxane sold under the tradename Volatile Silicone 7207 by Union Carbide or the tradename Silbione® 70045 V2 by Rhodia, decamethylcyclopentasiloxane sold under the tradename Volatile Silicone 7158 by Union Carbide or the tradename Silbione® 70045 V5 by Rhodia, or mixtures thereof.

Mention may also be made of cyclocopolymers of the dimethylsiloxane/methylalkylsiloxane type, which may be sold under the tradename Volatile Silicone FZ 3109 by Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50), and the mixture of octamethylcyclotetrasiloxane and oxy-1,1 '-bis(2,2,2',2',3,3'-hexatrimethylsilyloxy)neopentane.

Examples of linear volatile polydialkylsiloxanes containing 2 to 9 silicon atoms and having a viscosity of less than or equal to $5\times10^{-6}$ m$^2$/s at 25 degrees centigrade include a decamethyltetrasiloxane sold under the tradename SH 200 by Toray Silicone.

In certain embodiments, non-volatile polydialkylsiloxanes may be chosen from, for example polydimethylsiloxanes having trimethylsilyl end groups. The viscosity of the silicones is measured at 25 degrees centigrade according to ASTM standard 445 Appendix C.

Mention may be made, among these polydialkylsiloxanes, of the following commercial products:
 the Silbione® oils of the 47 and 70 047 series or the Mirasil® oils sold by Rhodia, for example, the oil 70 047 V 500 000;
 the oils of the Mirasil® series sold by Rhodia;
 the oils of the 200 series from the company Dow Corning®, such as DC200 with a viscosity of 60 000 mm2/s;
 the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

In certain embodiments, the liquid fatty substance may be chosen from $C_6$-$C_{16}$ alkanes; non-silicone oils of plant, mineral, or synthetic origin; liquid fatty alcohols; liquid fatty acids; liquid esters of a fatty acid and/or of a fatty alcohol; or mixtures thereof.

In certain embodiments, the liquid fatty substance may be chosen from liquid petroleum jelly, $C_6$-$C_{16}$ alkanes, mineral oil, polydecenes, liquid esters of a fatty acid and/or of a fatty alcohol, liquid fatty alcohols, or mixtures thereof.

In certain embodiments, the liquid fatty substance is mineral oil which may be commercially available from the supplier Sonneborn under the tradename Kaydol® Heavy White Mineral Oil, from the supplier Exxonmobil Chemical under the tradename Primol 352, from Sonneborn under the tradename Blandol®, from the supplier Armedsa under the tradename Aemoil M-302CG, or from the supplier Exxonmobil Chemical under the tradename Marcol® 82.

The liquid fatty substance is present in an amount ranging from about 1 to about 50% by weight, from about 2% to about 47% by weight, from about 3% to about 44% by weight, or from about 4% to about 40% by weight, relative to the total weight of the composition.

In some embodiments, the liquid fatty substance is present in an amount ranging from about 1% to about 50% by weight, from about 2% to about 47% by weight, from about 3% to about 44% by weight, or from about 4% to about 40% by weight, relative to the total weight of the first mixture.

If the at least one liquid fatty substance is present in a ready to use composition comprising the first mixture, the second mixture, and a solvent composition or developer, the liquid fatty substance is present in an amount ranging from about 1 to about 40% by weight, from about 5% to about 35% by weight, from about 10% to about 30% by weight, or from about 15% to about 25% by weight, relative to the total weight of the ready to use composition.

Silica Material

The compositions according to the disclosed embodiments comprise at least one silica material.

In certain embodiments, the silica material may comprise silica particles that are hydrophilic or hydrophobic silicas or mixtures thereof.

In other embodiments, the hydrophilic silica may include pure hydrophilic silica particles and particles which are wholly or partly coated with hydrophilic silica.

In other embodiments, the hydrophilic silica may be amorphous. It may be of pyrogenic or precipitated origin. It can also be in powder form or in an aqueous dispersion.

In certain embodiments, the hydrophilic silica is a fumed hydrophilic silica. The fumed hydrophilic silica may be obtained by continuous flame pyrolysis at 1000° C. of silicon tetrachloride, $SiCl_4$, in the presence of hydrogen and of oxygen. The precipitated silica is obtained by reacting an acid with a solution of alkali silicate, such as sodium silicate.

In other embodiments, the hydrophilic silica may be chosen from silicas having a specific surface area ranging from about 30 to about 500 m$^2$/g, a number-average particle size ranging from about 3 to about 50 nm, and a packed density ranging from about 40 to about 200 g/I. Such silicas include those sold by the company Degussa-Hijls under the tradenames Aerosil® 90, Aerosil® 130, Aerosil® 150, Aerosil® 200, Aerosil® 300, Aerosil® 380, Aerosil® OX50, and Aerosil® 320DS.

In other embodiments, the silica may be provided as an aqueous dispersion, for example a dispersion of colloidal silica, such as a colloidal dispersion of amorphous silica having a particle size of 14 nanometres, in water 30/70 sold under the tradename Bindzil® 30/220 by the company Eka Chemicals, or such as the product sold under the INCI name hydrated silica and tradename Elfadent SM 514 by the company Grace Davison.

In certain embodiments, the hydrophilic silica may be chosen from a particle comprising a silica surface, for example a particle totally or partially covered with silica, or a mineral particle totally or partially covered with silica. In other embodiments, the hydrophilic silica may be chosen from fumed silicas, for example those sold under the tradenames Aerosil® 200 and Aerosil® 300 by the company Degussa-Hijls.

In certain embodiments, the hydrophobic silica may be an amorphous hydrophobic silica of fumed origin. The amorphous hydrophobic silica of fumed origin is obtained from hydrophilic silica. Hydrophilic silica is obtained by continuous flame pyrolysis at 1000° C. of silicon tetrachloride, $SiCl_4$, in the presence of hydrogen and of oxygen. It is then made hydrophobic by treatment with halogenated silanes, alkoxysilanes, or silazanes. The hydrophobic silica differs from the starting hydrophilic silica by virtue of a lower silanol group density and a lower water vapor adsorption.

In certain embodiments, the hydrophobic silica may be chosen from silicas having a specific surface area ranging from about 50 to about 500 m$^2$/g, a number-average particle size ranging from about 3 to about 50 nm and a packed density ranging from about 40 to about 200 g/I or from about 50 to about 150 g/I. These silicas may be sold by the company Degussa-Hijls under the tradenames Aerosil® R202, Aerosil® R805, Aerosil® R812, Aerosil® R972, and Aerosil® R974.

In certain embodiments, the hydrophobic silica may be chosen from a particle totally or partially covered with hydrophobic silica, a mineral particle totally or partially covered with hydrophobic silica, such as pigments and metal oxides covered with hydrophobic silica. The hydrophobic silica may be chosen from the product sold under the tradename Aerosil® R972 by the company Degussa-Hijls.

Other examples of silica particles comprise silica powders that include:

- porous silica microspheres, for example those sold under the tradenames Sunsphere® H53 and Sunsphere® H33 by the company Asahi Glass and MSS-500-3H by the company Kobo;
- polydimethylsiloxane-coated amorphous silica microspheres, for example those sold under the tradename SA Sunsphere® H33 by the company Asahi Glass;
- amorphous hollow silica particles, for example those sold under the tradename Silica Shells by the company Kobo; and
- precipitated silica powders surface-treated with a mineral wax, such as precipitated silica treated with a polyethylene wax, and those sold under the tradename Acematt® OK 412 by the company Evonik-Degussa.

In certain embodiments, the silica particle may be chosen from hydrophobic silica aerogel particles. These hydrophobic silica aerogel particles may also be referred to herein as "aerogels."

Aerogels are ultra-light porous materials. They may be synthesized via a sol-gel process in a liquid medium and then dried, for example, by extraction with a supercritical fluid, such as supercritical $CO_2$. This type of drying makes it possible to avoid shrinkage of the pores and of the material. Other types of drying also make it possible to obtain porous materials starting from gel, namely cryodesiccation, which consists of solidifying the gel at a low temperature, subliming the solvent, and drying by evaporation. The materials obtained are referred to respectively as cryogels and xerogels.

In certain embodiments, the aerogel particles may be hydrophobic aerogel particles.

The term "hydrophobic aerogel particle" means any particle of the aerogel type having a water absorption capacity at the wet point of less than about 0.1 mL/g, i.e. less than 0.1 mL of water per 1 g of particle. The absorption capacity measured at the wet point, denoted Wp, corresponds to the amount of oil that needs to be added to 1 g of particles in order to obtain a homogeneous paste.

The following method is derived directly from the method for determining the oil uptake of a powder as described in standard NF T 30-022.

The wet point is measured according to the following protocol: A glass plate is placed on a balance and 1 g of aerogel is weighed out. A beaker containing the solvent and the liquid sampling pipette is placed on the balance. The solvent is gradually added to the powder, while the contents are regularly blended, for example every 3 to 4 drops, with a spatula. The mass of solvent required to reach the wet point is noted and the average of three tests are determined.

In other embodiments, the hydrophobic aerogel may be an organic, inorganic or organic-inorganic hybrid aerogel.

In certain embodiments, the organic aerogel may be based on a resin chosen from polyurethanes, resorcinol-formaldehyde, polyfurfuranol, cresol-formaldehyde, phenol-furfuranol, polybutadiene, melamine-formaldehyde, phenol-furfural, polyimides, polyacrylates, polymethacrylates, polyolefins, polystyrenes, polyacrylonitriles, phenol-formaldehyde, polyvinyl alcohol, dialdehydes, polycyanides, epoxys, celluloses, cellulose derivatives, chitosan, agar, agarose, alginate, starches, or mixtures thereof.

In other embodiments, the aerogel may be based on an organic-inorganic hybrid, for example silica-PMMA, silica-chitosan, or silica-polyether. U.S. Patent Publication No. 2005/0 192 366 and WO 2007/126 410 describe such organic-inorganic hybrid materials.

In certain embodiments, the hydrophobic aerogel particles may have a specific surface area per unit of mass (SM) ranging from about 200 to about 1500 $m^2/g$, from about 600 to about 1200 $m^2/g$, or from about 600 to about 800 $m^2/g$, and a size, expressed as the volume-mean diameter (D[0.5]), of less than about 1500 µm, or ranging from about 1 to about 30 µm, from about 5 to about 25 µm, from about 5 to about 20 µm, or from about 5 to about 15 µm.

In certain embodiments, the hydrophobic aerogel particles may have a specific surface area per unit of mass (SM) ranging from about 600 to about 800 $m^2/g$ and a size, expressed as the volume-mean diameter (D[0.5]), ranging from about 5 to about 20 µm or from about 5 to about 15 µm.

The specific surface area per unit of mass (SM) can be determined by the nitrogen absorption method, known as the BET (Brunauer-Emmett-Teller) method, described in The Journal of the American Chemical Society, Vol. 60, page 309, February 1938. The BET specific surface area corresponds to the total specific surface area of the particles under consideration.

The size of the hydrophobic aerogel particles can be measured by static light scattering using a commercial particle size analyzer such as the MasterSizer® 2000 machine from Malvern. The data is processed on the basis of the Mie scattering theory.

In other embodiments, the hydrophobic aerogel particles may have a tapped density ranging from about 0.02 $g/cm^3$ to about 0.10 $g/cm^3$ or from about 0.02 $g/cm^3$ to about 0.08 $g/cm^3$. This density may be assessed according to the following protocol, known as the tapped density protocol:

40 g of powder is poured into a measuring cylinder. The measuring cylinder is then placed on a Stay 2003 Stampf Volumeter and the measuring cylinder is subsequently subjected to a series of 2500 tapping actions. This operation is repeated until the difference in volume between two consecutive tests is less than 2%. The final volume Vf of tapped powder is measured directly on the measuring cylinder. The tapped density is determined by the ratio m/Vf, in this instance 40/Vf (Vf expressed in $cm^3$ and m in g).

In certain embodiments, the hydrophobic aerogel particles may have a specific surface area per unit of volume (SV) ranging from about 5 to about 60 $m^2/cm^3$, from about 10 to about 50 $m^2/cm^3$, or from about 15 to about 40 $m^2/cm^3$.

In certain embodiments, the hydrophobic aerogel particles may have an oil-absorbing capacity, measured at the wet point, ranging from about 5 to 18 mL/g, from about 6 to about 15 mL/g, or from about 8 to about 12 ml/g.

The absorption capacity measured at the wet point, denoted Wp, corresponds to the amount of oil that needs to be added to 100 g of particles in order to obtain a homogeneous paste. It is measured according to the "wet point" method or method for determining the oil uptake of a powder as described in standard NF T 30-022. It corresponds to the amount of oil adsorbed onto the available surface of the powder and/or absorbed by the powder by measurement of the wet point, described as follows:

2 g of powder is placed on a glass plate and oil, isononyl isononanoate, is then added dropwise. After the addition of 4 to 5 drops of oil to the powder, the oil and powder are mixed using a spatula. More oil is added until conglomerates of oil and powder have formed. From this point, the oil is added one drop at a time and the mixture is then triturated with the spatula. The addition of oil is stopped when a firm and smooth paste is obtained. This paste must be able to be spread over the glass plate without cracking or forming lumps. The volume Vs (expressed in ml) of oil used is then noted. The oil uptake corresponds to the ratio Vs/m.

In certain embodiments, the aerogel particles may be inorganic or hydrophobic silica aerogel particles. Silica aerogels are porous materials obtained by replacing the liquid component of a silica gel with air, for example, by drying.

In certain embodiments, the hydrophobic silica aerogel particles have a water absorption capacity at the wet point of less than about 0.1 mL/g or less than about 0.1 mL of water per 1 g of particle.

In certain embodiments, the hydrophobic silica aerogel particles have a specific surface area per unit of mass (SM) ranging from about 200 to about 1500 $m^2/g$, from about 600 to about 1200 $m^2/g$, or from about 600 to about 800 $m^2/g$, and a size, expressed as the volume-mean diameter (D[0.5]), of less than about 1500 µm, or ranging from about 1 to about 30 µm, from about 5 to about 25 µm, from about 5 to about 20 µm, or from about 5 to about 15 µm.

In certain embodiments, the hydrophobic silica aerogel particles have a specific surface area per unit of mass (SM) ranging from about 600 to about 800 $m^2/g$ and a size, expressed as the volume-mean diameter (D[0.5]), ranging from about 5 to about 20 µm or from about 5 to about 15 µm.

In certain embodiments, the hydrophobic silica aerogel particles may have a tapped density ranging from about 0.02 $g/cm^3$ to about 0.10 $g/cm^3$ or from 0.02 $g/cm^3$ to 0.08 $g/cm^3$.

In other embodiments, the hydrophobic silica aerogel particles have a specific surface area per unit of volume SV ranging from about 5 to about 60 $m^2/cm^3$, from about 10 to about 50 $m^2/cm^3$, or from about 15 to about 40 $m^2/cm^3$.

In other embodiments, the hydrophobic silica aerogel particles have an oil-absorbing capacity, measured at the wet point, ranging from about 5 to 18 ml/g, from about 6 to about 15 ml/g, or from about 8 to about 12 ml/g.

In certain embodiments, the hydrophobic silica aerogel particles are synthesized via a sol-gel process in a liquid medium and then dried, for example, by extraction with a supercritical fluid, such as supercritical $CO_2$. This type of drying makes it possible to avoid shrinkage of the pores and of the material.

In other embodiments, the hydrophobic silica aerogels are silylated silica aerogels (INCI name: silica silylate).

The term "hydrophobic silica" means any silica whose surface is treated with silylating agents, for example halogenated silanes such as alkylchlorosilanes, siloxanes, dimethylsiloxanes such as hexamethyldisiloxane, or silazanes, so as to functionalize the OH groups with silyl groups Si—Rn, for example trimethylsilyl groups.

In regards to the preparation of hydrophobic silica aerogel particles that have been surface-modified by silylation, reference may be made to U.S. Pat. No. 7,470,725.

In certain embodiments, the hydrophobic silica aerogel particles are surface-modified with trimethylsilyl groups.

In other embodiments, the hydrophobic silica aerogel may be chosen from an aerogel sold under the tradename VM-2260 (INCI name: Silica silylate) by Dow Corning®, the particles of which have a mean size of about 1000 microns and a specific surface area per unit of mass ranging from about 600 to about 800 $m^2/g$.

Mention may also be made of the aerogels sold by Cabot under the tradenames Aerogel TLD 201, Aerogel OGD 201 and Aerogel TLD 203, Enova® Aerogel MT 1100 and Enova® Aerogel MT 1200.

In other embodiments, the silica particles may also be natural and non-treated. For example, those known under the tradenames Sillitin® N85, Sillitin® N87, Sillitin® N82, Sillitin® V85, and Sillitin® V88, commercially available from the company Hoffmann Mineral.

According to other embodiments, the silica particles may be hydrated silica, for example, that sold under the tradename Elfadent SM 514 by the company Grace Davison.

According to other embodiments, the silica particles may be hydrophobic silica aerogel particles or aerogel sold under the tradename VM-2270 (INCI name: Silica silylate, 98% active), by the company Dow Corning®, the particles of which have a mean size ranging from about 5 to about 15 microns, a specific surface area per unit of mass ranging from about 600 to about 800 $m^2/g$, and an oil uptake equal to about 1080 ml/100 g.

In certain embodiments, the silica material may employ at least one of the different types of the above-described silica particles.

The silica material is present in an amount ranging from about 0.5% to about 40% by weight, from about 0.5% to about 30% by weight, from about 0.5% to about 20% by weight, from about 0.5% to about 10% by weight, or from about 0.5% to about 6% by weight, relative to the total weight of the composition.

In some embodiments, the silica material is present in an amount ranging from about 0.5% to about 40% by weight, from about 0.5% to about 30% by weight, from about 0.5% to about 20% by weight, from about 0.5% to about 10% by weight, or from about 0.5% to about 6% by weight, relative to the total weight of the first mixture.

In certain embodiments, the silica material may be chosen from hydrophobic silica aerogels and may be present in the composition in an amount ranging from about 0.5 to about 3% by weight, about 3%, about 2.5%, about 2%, about 1.5%, about 1% or about 0.5% by weight, relative to the total weight of the composition.

In other embodiments, the silica material may be chosen from hydrophobic silica aerogels and may be present in the composition in an amount ranging from about 0.5 to about 3% by weight, about 3%, about 2.5%, about 2%, about 1.5%, about 1% or about 0.5% by weight, relative to the total weight of the first mixture.

Oxidizing Composition

The second mixture, comprising the at least one oxidizing component, at least one acrylic polymer, and at least one chelant compound, may also be referred to as an oxidizing mixture or oxidizing composition.

In certain embodiments, the oxidizing composition is aqueous or is in the form of an emulsion. In another embodiment, the oxidizing composition is substantially anhydrous.

The term "substantially anhydrous" means that the oxidizing composition is either completely free of water or contains no appreciable amount of water, for example, no more than about 5% by weight, no more than about 2% by weight, or no more than about 1% by weight, relative to the total weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, for example water, organic solvents, or mixtures thereof.

When the oxidizing composition is substantially anhydrous, the oxidizing composition may comprise at least one solvent chosen from organic solvents. These organic solvents may include alcohols such as ethanol, isopropyl alcohol, propanol, benzyl alcohol, or phenyl ethyl alcohol; glycols and glycol ethers such as propylene glycol, hexylene glycol, ethylene glycol monomethyl, monoethyl or monobutyl ether; propylene glycol and its ethers such as propylene glycol monomethyl ether; butylene glycol; dipropylene glycol; diethylene glycol alkyl ethers such as diethylene glycol monoethyl ether and monobutyl ether; ethylene glycol; propylene glycol; butylene glycol, hexylene glycol; propane diol; glycerin; hydrocarbons such as straight chain hydrocarbons, mineral oil, polybutene, hydrogenated polyisobutene, hydrogenated polydecene, polydecene, squalane, petrolatum, or isoparaffins; or mixtures thereof.

In certain embodiments, the organic solvent may be volatile or non-volatile compounds. The organic solvent may, for example, be present in the composition in an amount ranging from about 0.5% to about 70% by weight, from about 2% to about 60% by weight, or from about 5 to about 50% by weight, relative to the total weight of the oxidizing composition.

The oxidizing composition may be in the form of a powder, gel, liquid, foam, lotion, cream, mousse, or emulsion.

Oxidizing Component

The compositions according to the disclosed embodiments comprise at least one oxidizing component.

The oxidizing component may be chosen from peroxides, persulfates, perborates, percarbonates, alkali metal bromates, ferricyanides, peroxygenated salts, or mixtures thereof. Oxidizing components that may also be used include at least one redox enzyme such as laccases, peroxidases, and 2-electron oxidoreductases, such as uricase, where appropriate in the presence of their respective donor or co-factor. Oxygen in the air may also be an oxidizing component.

In certain embodiments, the oxidizing component is hydrogen peroxide present in an aqueous solution whose titre may range from about 1 to about 40 volumes, from about 5 to about 40 volumes or from about 5 to about 20 volumes.

In certain embodiments, the oxidizing component may be a persulfate and/or a monopersulfate, for example, potassium persulfate, sodium persulfate, ammonium persulfate, or mixtures thereof. In other embodiments, the oxidizing component may be hydrogen peroxide, potassium persulfate, sodium persulfate, or mixtures thereof. In other embodiments, the oxidizing component is hydrogen peroxide.

The at least one oxidizing component is present in an amount ranging from about 1% to about 40% by weight, from about 2% to about 35% by weight, from about 3% to about 30% by weight, from about 4% to about 25% by weight, or from about 5% to about 20% by weight, relative to the total weight of the composition.

In some embodiments, the at least one oxidizing component is present in an amount ranging from about 1% to about 40% by weight, from about 2% to about 35% by weight, from about 3% to about 30% by weight, from about 4% to about 25% by weight, or from about 5% to about 20% by weight, relative to the total weight of the second mixture, or oxidizing composition.

Acrylic Polymer

The compositions according to the disclosed embodiments comprise at least one acrylic polymer.

The acrylic polymer may be chosen from crosslinked acrylic polymers. Crosslinked acrylic polymers may be selected from modified or unmodified carboxyvinyl polymers, such as copolymers of acrylic acid and of C10-C30 alkyl acrylate or methacrylate, for example the products sold under the tradenames Carbopol® and Pemulen™ (INCI names: carbomer, acrylates/C10-30 alkyl acrylate crosspolymer) by the company Lubrizol, or the crosslinked sodium polyacrylate sold under the tradename Cosmedia® SP by the company Cognis (BASF).

The crosslinked acrylic polymer may be chosen from sodium polyacrylate, carbomer, acrylates/C10-30 alkyl acrylate crosspolymer, or mixtures thereof.

In certain embodiments, the crosslinked acrylic polymer is sodium polyacrylate.

In other embodiments, the crosslinked acrylic polymer is chosen from acrylates/C10-30 alkyl acrylate crosspolymer.

The acrylic polymer is present in an amount ranging from about 0.5% to about 30% by weight, from about 0.5% to about 20% by weight, from about 0.5% to about 10% by weight, or from about 0.5% to about 5% by weight, relative to the total weight of the composition.

In some embodiments, the acrylic polymer is present in an amount ranging from about 0.5% to about 30% by weight, from about 0.5% to about 20% by weight, from about 0.5% to about 10% by weight, or from about 0.5% to about 5% by weight, relative to the total weight of the second mixture, or oxidizing composition.

Chelant Compound

The compositions according to the disclosed embodiments comprise at least one chelant compound.

The chelant compound may be chosen from ethylene diamine tetraacetic acid (EDTA) and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; N-2-hydroxyethyliminodiacetic acid and its salts; ethyleneglycol-bis(beta-amino ethyl ether)-N,N-tetraacetic acid; or pentasodium aminotrimethylene phosphonate. The salts may be chosen from salts with organic or inorganic cations. In some embodiments, the inorganic cation may be chosen from potassium, sodium or lithium.

In certain embodiments, the chelant compound may be a salt of EDTA, such as sodium, lithium, potassium or guanidine EDTA.

In other embodiments, the chelant compound may be combined with at least one sequestering agent.

The chelant compound is present in an amount ranging from about 0.1% to about 10% by weight, from about 0.3% to about 8% by weight, from about 0.5% to about 6% by weight, or from about 0.7% to about 4% by weight, or from about 0.8% to about 2% by weight, relative to the total weight of the composition.

In some embodiments, the chelant compound is present in an amount ranging from about 0.1% to about 10% by weight, from about 0.3% to about 8% by weight, from about 0.5% to about 6% by weight, or from about 0.7% to about 4% by weight, or from about 0.8% to about 2% by weight, relative to the total weight of the second mixture, or oxidizing composition.

Wax

The compositions according to the disclosed embodiments may further comprise at least one wax. Waxes may also be known as solid lipids.

The wax may be solid or semisolid at room temperature. The wax may have a melting point at or greater than about 30° C., from about 35° C. to about 250° C., or from about 40° C. to about 100° C. The wax has a reversible change of solid/liquid state. The melting point of a wax in solid form is the same as the freezing point of its liquid form, and depends on such factors as the purity of the substance and the surrounding pressure. The melting point is the temperature at which a solid and its liquid are in equilibrium at any fixed pressure. A solid wax begins to soften at a temperature close to the melting point of the wax. With increasing temperature, the wax continues to soften/melt until the wax becomes completely liquid at a standard atmospheric pressure. At this stage, an actual melting point value is given for the material under consideration. When heat is removed, the liquefied wax material begins to solidify until the material is back in solid form. By bringing the wax material to the liquid state, it is possible to make it miscible with other materials, such as oils, and to form a microscopically homogeneous mixture. When the temperature of the mixture is brought to room temperature, recrystallization of the wax with the other materials in the mixture may be obtained.

The melting points of the wax may be determined according to known methods or apparatus such as by differential scanning calorimetry, Banc Koffler device, melting point apparatus, or slip melting point measurements.

In other embodiments, the wax may be chosen from waxes that have hardness values ranging from about 0.001 MPa to about 15 MPa, from about 1 MPa to about 12 MPa, or from about 3 MPa to about 10 MPa.

The hardness of the wax may be determined by any known method or apparatus such as by needle penetration or by using a durometer or texturometer.

In certain embodiments, the wax may be chosen from natural waxes and synthetic waxes.

Natural waxes include animal, vegetable/plant, mineral, or petroleum derived waxes. They are typically esters of fatty acids and long chain alcohols. Wax esters are derived from a variety of carboxylic acids and a variety of fatty alcohols.

In other embodiments, the wax may be chosen from beeswax, hydrogenated alkyl olive esters such as hydrogenated myristyl olive esters and hydrogenated stearyl olive esters commercially available under the tradename Phytowax® olive from the supplier Sophim, carnauba wax, candelilla wax, ouricoury wax, Japan wax, cork fiber wax or sugar cane wax, rice wax, rice bran wax, montan wax, paraffin wax, lignite wax or microcrystalline wax, ceresin or ozokerite, palm kernel glycerides/hydrogenated palm glycerides, palm butter, sumac wax, citrus *aurantium dulcis* peel wax, *theobroma grandiflorum* seed butter, *helianthus annuus* seed wax, siliconyl candellila wax, hydrogenated oils such as hydrogenated castor oil or jojoba oil, sugarcane, retamo, bayberry, soy, castor, esparto, hydroxyoctacosanyl hydroxystearate, Chinese wax, cetyl palmitate, lanolin, shellac, spermaceti, hydrogenated castor wax, synthetic waxes such as those of the hydrocarbon type, polyethylene waxes obtained from the polymerization or copolymerization of ethylene, polypropylene waxes, Fischer-Tropsch® waxes, esters of fatty acids such as octacosanyl stearate, glycerides which are solid at temperatures of above 35° C., poly(di) methylsiloxane esters which are solid at 30° C. and whose ester chain comprise at least 10 carbon atoms, di(1,1,1-trimethylolpropane) tetrastearate which is sold or manufactured by Heterene under the tradename HEST 2T-4S, polyglycerol beeswax, siliconyl beeswax, or mixtures thereof.

In certain embodiments, the wax may be chosen from polytetrafluoroethylene (PTFE), amides, bioplastics, PVP/eicosene copolymer, tricontanyl PVP, or C20-40 alkyl stearate.

In other embodiments, the wax may be chosen from C20-40 di- and triglycerides, including those which contain unsaturated fatty acids, C20-40 fatty alcohols, C2-40 fatty amines and their compounds, or sterols.

In other embodiments, the wax may be chosen from silicone waxes or silicone resin waxes, such as alkyl- or alkoxydimethicones having an alkyl or alkoxy chain ranging from 10 to 45 carbon atoms. Examples of silicone waxes are silsesquioxane resin waxes such as C30-45 alkyldimethylsilyl propylsilsesquioxane, which are available under the tradename DOW CORNING® SW-8005 C30 Resin Wax, from the company Dow Corning®.

In other embodiments, the wax may be chosen from those having a melting point greater than about 35° C., for example beeswax, commercially available from various suppliers; hydrogenated stearyl olive ester, commercially available from the supplier Sophim under the tradename Phytowax® Olive 18 L 57; hydrogenated myristyl olive ester, commercially available from the supplier Sophim under the tradename Phytowax® Olive 14 L 48; VP/eicosene copolymer, commercially available from the supplier ISP under the tradenames Antaron® V 220 or Ganex® V 220F; or ditrimethyloylpropane tetrastearate, commercially available from the supplier Heterene under the tradename, HEST 2T-4S.

In other embodiments, the wax may be chosen from soft waxes or hard waxes. Soft waxes may be defined as those waxes having a melting point below about 70° C. or below about 60° C. Hard waxes may be defined as those waxes having melting point of greater than or equal to about 70° C. or greater than or equal to about 60° C.

In other embodiments, the wax is carnauba wax, also referred to as *copernicia cerifera* wax, which may be commercially available from the supplier Micro Powders, Inc. under the tradename Microcare 350.

In other embodiments, the wax may be chosen from polyethylene wax, synthetic wax, polytetrafluoroethylene (PTFE), or mixtures thereof, which may be commercially available from the supplier Micro Powders, Inc. under the tradenames Microsilk 418, Microsilk 419, and Microsilk 920.

The wax is present in an amount ranging from about 0.1% to about 30% by weight, from about 0.5% to about 20% by weight, or from about 1% to about 10% by weight, relative to the total weight of the composition.

In some embodiments, the wax is present in an amount ranging from about 0.1% to about 30% by weight, from about 0.5% to about 20% by weight, or from about 1% to about 10% by weight, relative to the total weight of the first mixture and/or the second mixture.

In certain embodiments, the wax is present in an amount ranging from about 3% to about 6% by weight, about 6%, about 5%, about 4%, about 3%, about 2%, or about 1%, by weight, relative to the total weight of the composition.

In some embodiments, the wax is present in an amount ranging from about 3% to about 6% by weight, about 6%, about 5%, about 4%, about 3%, about 2%, or about 1%, by weight, relative to the total weight of the first mixture and/or the second mixture.

pH

In certain embodiments, the pH of the hair color-altering composition may range from about 8 to about 12, or from about 10 to about 11.

All numbers expressing pH values are to be understood as being modified in all instances by the term "about" which encompasses up to ±3%.

Surfactants

The compositions according to the disclosed embodiments may further comprise at least one surfactant selected from anionic surfactants, nonionic surfactants, amphoteric or zwitterionic surfactants, cationic surfactants, or mixtures thereof.

The surfactant may be present in the composition in an amount ranging from about 0.01% to about 40% by weight, from about 0.05% to about 30% by weight, from about 0.1% to about 30% by weight, or from about 1% to about 20% by weight, relative to the total weight of the composition.

In some embodiments, the surfactant may be present in the composition in an amount ranging from about 0.01% to about 40% by weight, from about 0.05% to about 30% by weight, from about 0.1% to about 30% by weight, or from about 1% to about 20% by weight, relative to the total weight of the first mixture and/or the second mixture.

Anionic Surfactants

The term "anionic surfactant" is understood to mean a surfactant comprising, as ionic or ionizable groups, only anionic groups. These anionic groups may be chosen from the following groups: CO2H, CO2-, SO3H, SO3-, OSO3H, OSO3-, H2PO3, —HPO3-, —PO32-, —H2PO2, =HPO2, —HPO2-, =PO2-, =POH and =PO—.

In certain embodiments, the anionic surfactant may be chosen from alkyl sulfates, alkyl ether sulfates, alkylamido ether sulfates, alkylaryl polyether sulfates, monoglyceride sulfates, alkylsulfonates, alkylamidesulfonates, alkylaryl-sulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alykyl ether carboxylates, alkyl sulfosuccinamates, acyl isethionates and N-acyl taurate, monoalkyl esters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids and the corresponding non-salified forms of all these compounds, the alkyl and acyl groups of all these compounds comprising from 6 to 24 carbon atoms and the aryl group denoting a phenyl group, or mixtures thereof.

These compounds may be oxyethylenated and comprise from 1 to 50 ethylene oxide units or from 1 to 10 ethylene oxide units.

The salts of C6-C24 alkyl monoesters of polyglycoside-polycarboxylic acids may be chosen from C6-C24 alkyl polyglycoside-citrates, C6-C24 alkyl polyglycoside-tartrates or C6-C24 alkyl polyglycoside-sulfosuccinates.

The acyl lactylates may have an acyl group comprising from 8 to 20 carbon atoms.

When the anionic surfactant is in the salt form, it may be chosen from alkali metal salts such as sodium salt or potassium salt, ammonium salt, amine salts such as aminoalcohol salts, or alkaline earth metal salts such as magnesium salt.

In certain embodiments, the anionic surfactant may be alkali metal or alkaline earth metal salts such as sodium salts or magnesium salts.

In other embodiments, the anionic surfactant may be chosen from C6-24 alkyl sulfates, C6-24 alkyl ether sulfates, acyl glutamates, or C6-C24 alkyl ether carboxylates.

In other embodiments, the anionic surfactant may be chosen from alkali metal, ammonium, aminoalcohol, alkaline earth metal salts, or mixtures thereof.

In other embodiments, the anionic surfactant may be chosen from C12-20 alkyl sulfates, C12-20 alkyl ether sulfates comprising from 2 to 20 ethylene oxide units, acyl glutamates, C12-C20 alkyl ether carboxylates, alkali metal, ammonium, aminoalcohol, alkaline earth metal salts, or mixtures thereof.

Nonionic Surfactants

The non-ionic surfactant may be chosen from polyethoxylated and/or polypropoxylated alkyl phenols, alpha-diols, or alcohols. In some embodiments, the non-ionic surfactant may comprise fatty chains comprising, for example, from 8 to 18 carbon atoms, and a number of ethylene oxide and/or propylene oxide groups ranging from 2 to 50.

In other embodiments, the non-ionic surfactant may be chosen from copolymers of ethylene oxide and of propylene oxide; condensates of ethylene oxide and/or of propylene oxide with fatty alcohols; polyethoxylated fatty amides comprising, for example, from about 2 to about 30 moles of ethylene oxide; polyglycerolated fatty amides comprising about 1 to about 5 glycerol groups or about 1.5 to about 4 glycerol groups; polyethoxylated fatty amines comprising, for example, from about 2 to about 30 moles of ethylene oxide; oxyethylenated fatty acid esters of sorbitan comprising, for example, from about 2 to about 30 moles of ethylene oxide; fatty acid esters of sucrose; fatty acid esters of polyethylene glycol; alkylpolyglycosides; N-alkylglucamine derivatives; amine oxides such as C10-C14 alkyl amine oxides; N-acylaminopropylmorpholine oxides; or mixtures thereof.

Amphoteric or Zwitterionic Surfactants

The amphoteric or zwitterionic surfactant may be a derivative of optionally quaternized secondary or tertiary aliphatic amines comprising at least one anionic group, for example, a carboxylate, sulfonate, sulfate, phosphate or phosphonate group, and in which at least one aliphatic group is a linear or branched chain comprising from 8 to 22 carbon atoms.

Mention may be made of (C8-C20) alkyl betaines, sulfobetaines, (C8-C20) alkylamido (C1-C6) alkyl betaines such as cocoamidopropyl betaine, or (C8-C20) alkylamido (C1-C6) alkyl sulfobetaines.

Mention may also be made of optionally quaternized secondary or tertiary aliphatic amines such as disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid.

A cocoamphodiacetate is sold by Rhodia under the tradename Miranol® C2M Concentrate. Additionally, a sodium diethylaminopropyl cocoaspartamide is sold by Chimex under the tradename Chimexane HB.

In certain embodiments, the amphoteric or zwitterionic surfactant may be chosen from (C8-C20) alkyl betaines, (C8-C20) alkylamido (C1-C6) alkyl betaines and (C8-C20) alkylamphodiacetates, the sodium salt of diethylaminopropyl laurylaminosuccinamate, or mixtures thereof.

In other embodiments, the amphoteric or zwitterionic surfactant may be chosen from cocoylamidopropyl betaine, cocoyl betaine, cocoamphodiacetate, or mixtures thereof.

Cationic Surfactants

The cationic surfactant may be chosen from salts of optionally polyoxyalkylenated primary, secondary and tertiary fatty amines, quaternary ammonium salts such as tetra alkyl ammonium, alkylamidoalkyltrialkyl ammonium, trialkylbenzyl ammonium, trialkylhydroxyalkyl ammonium, alkylpyridinium chlorides and bromides, imidazoline derivatives, cationic amine oxides, or mixtures thereof.

Auxiliary Ingredients

The compositions according to the disclosed embodiments may further comprise any auxiliary ingredient usually used in the field under consideration, selected, for example, from organic amines, carbonate compounds, emulsifying agents, fillers, pigments, conditioning agents, moisturizing agents, additional viscosity or thickening agents, shine agents, sequestering agents, fragrances, preservatives, pH modifiers/neutralizing agents, stabilizers, or mixtures thereof.

It is a matter of routine operation for a person skilled in the art to adjust the nature and amount of the additives present in the compositions such that the desired cosmetic properties and stability properties thereof are not thereby affected.

If present in the composition, these auxiliary ingredients may constitute from about 0.5% to about 30% by weight, from about 1%')/0 to about 15% by weight, or from about 1% to about 10% by weight, relative to the total weight of the composition.

In some embodiments, these auxiliary ingredients constitute from about 0.5% to about 30% by weight, from about 1%')/0 to about 15% by weight, or from about 1% to about 10% by weight, relative to the total weight of the first mixture and/or the second mixture.

In certain embodiments, the composition may further comprise an alkaline material comprising hydroxide-containing compounds, starch, silica material, liquid fatty substance, acrylic polymer, or chelant compound. In certain embodiments, the composition may further comprise a non-starch, non-acrylic polymer, clay, surfactant, or auxiliary ingredient.

In certain embodiments, the composition is essentially free of water.

The composition may be mixed with varying amounts of the developer to obtain a ready to use composition with properties suitable for a particular use.

The term "developer" as used herein refers to any developer used and known in the art.

The term "ready to use composition" as used herein refers to the composition that is to be applied onto hair and comprises the hair color-altering composition and the developer. Generally, the ready to use composition is to be prepared by the consumer or hair dresser on the day that the hair is to be straightened or relaxed. It can be applied onto hair immediately after it is prepared. There could also be a certain period of time before the ready to use composition is applied onto hair from the time of preparation of said composition, such as from between about 2 minutes to about 60 minutes, or such as from between about 2 minutes to about 30 minutes. In certain embodiments, the resulting ready to use composition comprises the hair color-altering composition and the developer in a weight ratio ranging from about 1:3 to about 1:4.

In certain embodiments, the weight ratio of the hair color-altering composition to the developer in the ready to use composition is about 1:3.

In certain embodiments, the weight ratio of the hair color-altering composition to the developer in the ready to use composition is about 1:4.

The ready to use composition has a viscosity ranging from about 11830 cps to about 21215 cps, from about 14175 cps to about 18870 cps, or from about 16520 cps to about 18870 cps.

The ready to use composition has a pH of greater than about 7, and ranges from about 9 to about 14, from about 10 to about 14, from about 11 to about 13.8, from about 12 to about 13.8, or from about 12.6 to about 13.6.

In certain embodiments, the ready to use composition has a viscosity ranging from about 11830 cps to about 21215 cps and a pH ranging from about 9 to about 14.

In certain embodiments, the ready to use composition has a viscosity ranging from about 14175 cps to about 18870 cps and a pH ranging from about 12.6 to about 13.6.

All numbers expressing pH values are to be understood as being modified in all instances by the term "about" which encompasses up to +/−3%. For example, a pH value of about 7.0 refers to 7+/−0.21.

Viscosity in cps was measured by a Mettler RM 180 Rheomat, spindle #3 at 25° C.

The hair color-altering composition is stable such that the activity or efficacy of the alkaline material is preserved until the composition is ready to be used or mixed with the developer.

In addition, the hair color-altering composition is stable over time due to minimal moisture content; it can be stored for several months without modification.

The hair color-altering composition was also surprisingly and unexpectedly discovered to be a free flowing powder that is easy to handle, is easily pourable, has non-sticky and non-clinging properties, and does not exhibit visible clumping. The hair color-altering composition remains free flowing after packaging and storage.

Kit and Method of Altering the Color of Hair

A further embodiment includes a hair color-altering "kit" or multi-compartment device in which a first compartment comprises a first mixture as described above and a second compartment comprises a second mixture as described above Certain embodiments concern a method of altering the color of hair, the method comprising the steps of: mixing a hair color composition with a developer, wherein the hair color composition comprises a first mixture and a second mixture, and applying the resulting system to the hair.

Upon application of the composition and after an optional resting or leave-on time on the hair, for example, ranging from about 1 to about 60 minutes, from about 5 to about 45 minutes, from about 5 to about 20 minutes, from about 10 to about 20 minutes, or about 20 minutes, the hair is rinsed, optionally washed with shampoo, optionally rinsed again, optionally washed with a hair conditioning composition, optionally rinsed again, and then dried or left to dry. The shampoo and hair conditioning composition can be any conventional hair shampoo and conditioner products.

In addition, independent of the embodiment use, the mixture or composition present on the fibers or hair, resulting from the extemporaneous mixing of the compositions, or from the successive application of the hair color base and oxidizing compositions, is left in place for a time ranging from about 1 to about 60 minutes, from about 5 to about 45 minutes, from about 5 to about 20 minutes, from about 10 to about 20 minutes, or for about 20 minutes.

The process of lifting and/or altering the color of hair is carried out at a temperature ranging from room temperature to about 80° C. or room temperature to about 60° C.

EXAMPLES

The following Examples are intended to be non-restrictive and explanatory only, with the scope of the disclosed embodiments.

The ingredient amounts in the compositions/formulas described below are expressed in % by weight, based on the total weight of the composition before it is mixed with a developer.

Example 1

| Ingredients | % by weight of ingredient |
| --- | --- |
| Potassium Persulfate | 40.00 |
| Sodium Persulfate | 13.00 |
| Sodium Silicate | 27.00 |
| EDTA | 0.80 |
| Polyethylene Wax | 1.51 |
| PVP | 0.99 |
| Sodium Polyacrylate | 0.825 |
| Mineral Oil | 4.00 |
| Sodium Lauryl Sulfate | 3.50 |
| Silicate Silylate | 0.50 |
| Corn Starch | 6.88 |
| Fragrance (V-Lights) | 1.00 |
| | 100.00 |

Example 1 was prepared according to the protocol as follows:

The starch and mineral oil was added into a 1 Kg beaker. The ingredients in the beaker were mixed on the Rayneri at 200-300 RPM for 2 minutes resulting in a white liquid mixture. The silica material was added slowly and carefully to the mixture and the mixture began to turn into a powder, also called a powdered oil system. The bottom of the beaker was scraped to ensure that all the oil was absorbed. The mixing speed was increased to 400-500 RPM and mixing was continued for 5 minutes. The resulting powdered oil system was a free-flowing powder. The rest of the ingredients, except the fragrance, were combined in a separate beaker and mixed with the Rayneri at 200-300 RPM for 20 minutes. The powdered oil system was slowly added to the rest of the ingredients. The combined mixture was mixed for 10 minutes. The fragrance was added to the mixture. The final mixture was mixed for 2 minutes.

Example 2

| Ingredients | % by weight of ingredient |
| --- | --- |
| Potassium Persulfate | 14.38 |
| Sodium Persulfate | 5.00 |
| Sodium Silicate | 7.00 |
| EDTA | 0.80 |
| Polyethylene Wax | 1.51 |
| PVP | 0.99 |
| Sodium Polyacrylate | 0.825 |
| Mineral Oil | 40.00 |
| Sodium Lauryl Sulfate | 1.50 |
| Silicate Silylate | 6.00 |
| Corn Starch | 21.00 |
| Fragrance (V-Lights) | 1.00 |
| | 100.00 |

Example 2 was prepared according to the protocol described above for Example 1.

For measuring the degree of change in the color of hair (e.g. degree of lightening/lifting (L) of color or color deposit) after treating the hair, the color of each swatch was measured with a Minolta CM2600d spectrocolorimeter (specular components included, 10 degrees angle, illuminant D65) in the CIEL*a*b* system. According to this system, the greater the value of L, the lighter or less intense the color. Conversely, the lower the value of L, the darker or more intense the color (this can also indicate greater color deposit when the composition contains colorants).

The compositions of Example 1 and Example 2 are each mixed with an oil-rich developer to form a 2-part bleach system, wherein the hair color-altering composition and the oil-rich developer are in a 1 to 3 ratio.

Comparative Example 1 comprises 54.57% persulfate and 1.98% mineral oil, which is then mixed with a booster and an oil-rich developer to form a 3-part bleach system, wherein Comparative Example 1, the booster, and the developer are in a 22:25:75 ratio.

TABLE 1

| % by weight | % persulfate | % mineral oil |
| --- | --- | --- |
| Example 1 | 53.00 | 4.00 |
| Example 2 | 19.38 | 40.00 |
| Comparative Example 1 | 54.57 | 1.98 |

Table 1 compares the percent by weight of persulfate and mineral oil present in various embodiments of the disclosure.

Each of the resulting bleach systems are applied to swatches of natural level 3 hair and natural level 6 hair.

FIG. 1 is a graph that compares lift studies done at natural level 3, according to various embodiments of the disclosure. Degree of lift, as shown on the Y axis, is measured in L. Time, as shown on the X axis, is measured in minutes. High amounts of persulfate are used in bleaching systems to lift the color of the hair. However, higher amounts of persulfate in a bleaching system may lead to negative consequences, for example damage to the hair and/or scalp. Examples 1 and 2 each comprise a higher amount of mineral oil and a lesser amount of persulfate than Comparative Example 1. Referring to FIG. 1, the degree of lift by using each of Example 1 and Example 2 is comparable to the degree of lift exhibited by Comparative Example 1.

Figure 2:
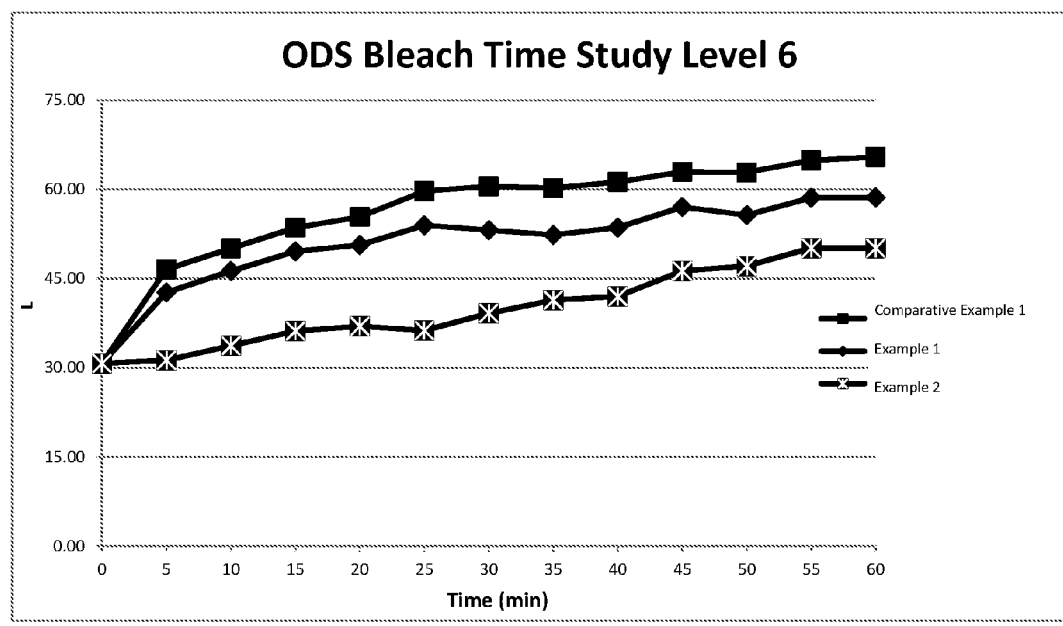
FIG. 2 is a graphical representation of lift studies for various hair color-altering systems, according to the exemplary embodiments of the disclosure.

FIG. 2 is a graph that compares lift studies done at natural level 6, according to various embodiments of the disclosure. Degree of lift, as shown on the Y axis, is measured in L. Time, as shown on the X axis, is measured in minutes. Similar to the lift studies done at natural level 3, Example 1 and Example 2 each produced a degree of lift comparable to the degree of lift exhibited by Comparative Example 1 despite a lower amount of persulfate than Comparative Example 1.

As set forth herein, various aspects of the disclosure are described with reference to the exemplary embodiments and/or the accompanying drawings in which exemplary embodiments are illustrated. The disclosed embodiments may, however, be embodied in many different forms and should not be construed as limited to the exemplary embodiments shown in the drawings or described herein. It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It will also be understood that, as used herein the terms "the," "a," or "an," mean "at least one," and should not be limited to "only one" unless explicitly indicated to the contrary. Thus, for example, reference to "a pore former" includes examples having two or more pore formers unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

What is claimed is:

1. A hair color-altering composition comprising:
    a first mixture comprising:
        from about 1% to about 50% of at least one starch;
        from about 1% to about 50% of at least one liquid fatty substance; and
        from about 0.5% to about 40% of at least one silica material;
        wherein the first mixture is free-flowing powdered oil mixture;
    and
    a second mixture comprising:
        from about 1% to about 40% of at least one oxidizing agent;
        from about 0.5% to about 30% of at least one acrylic polymer; and
        from about 0.1% to about 10% of at least one chelant compound;
    wherein the at least one oxidizing agent and at least one liquid fatty substance are present in a ratio ranging from about 0.48 to about 13.25,
    all weights above relative to the total weight of the hair color composition prior to mixing with a developer.

2. The hair color-altering composition according to claim 1, wherein the at least one starch is chosen from starches derived from corn, potato, sweet potato, pea, barley, wheat, rice, oat, sago, tapioca and sorghum; hydrolyzed starches chosen from dextrin and maltodextrin; modified starches; or mixtures thereof.

3. The hair color-altering composition according to claim 1, wherein the at least one starch is chosen from corn starch, potato starch, dextrin, maltodextrin, or mixtures thereof.

4. The hair color-altering composition according to claim 1, wherein the at least one liquid fatty substance is chosen from $C_6$-$C_{16}$ alkanes, non-silicone oils of plant, mineral or synthetic origin, liquid fatty alcohols, liquid fatty acids and liquid esters of a fatty acid and/or of a fatty alcohol, or mixtures thereof.

5. The hair color-altering composition according to claim 1, wherein the at least one liquid fatty substance is a mineral oil.

6. The hair color-altering composition according to claim 1, wherein the at least one silica material comprises silica particles chosen from hydrated silica, hydrophobic silica aerogel particle, or mixtures thereof.

7. The hair color-altering composition according to claim 1, wherein the at least one oxidizing agent is chosen from peroxides, persulfates, perborates, percarbonates, alkali metal bromates, ferricyanides, peroxygenated salts, or mixtures thereof.

8. The hair color-altering composition according to claim 1, wherein the at least one oxidizing agent is chosen from persulfate and monopersulfate.

9. The hair color-altering composition according to claim 1, wherein the at least one acrylic polymer is a crosslinked acrylic polymer.

10. The hair color-altering composition according to claim 1, wherein the crosslinked acrylic polymer is selected from sodium polyacrylate, carbomer, acrylates C10-30 alkyl acrylate crosspolymer, or mixtures thereof.

11. The hair color-altering composition according to claim 1, wherein the at least one chelant compound is selected from ethylenediaminetetraacetic acid (EDTA), and its salts; N-(hydroxyethyl) ethylene diamine triacetic acid and its salts; aminotrimethylene phosphonic acid and its salts; diethylenetriamine-pentaacetatic acid and its salts; lauroyl ethylene diamine triacetic acid and its salts; nitrilotriacetic acid and its salts; iminodisuccinic acid and its salts; tartaric acid and its salts; citric acid and its salts; N-2-hydroxyethyliminodiacetic acid and its salts; ethyleneglycol-bis(beta-amino ethyl ether)-N,N-tetraacetic acid; or pentasodium aminotrimethylene phosphonate, or mixtures thereof.

12. The hair color-altering composition according to claim 1, further comprising from about 0.1% to about 30% of at least one wax.

13. The hair color-altering composition according to claim 1, further comprising at least one surfactant selected from anionic surfactants, nonionic surfactants, amphoteric surfactants or mixtures thereof.

14. The hair color-altering composition according to claim 1, further comprising at least one ingredient chosen from organic amines, carbonate compounds, emulsifying agents, fillers, pigments, conditioning agents, moisturizing agents, additional viscosity or thickening agents, shine agents, sequestering agents, fragrances, preservatives, pH modifiers/neutralizing agents, stabilizers, or mixtures thereof.

15. The hair color-altering composition according to claim 1, having a pH in the range of about 8.5 to about 10.

16. A method for altering the color of hair, comprising:
    mixing a hair color composition with a developer to form a system, the hair color composition comprising:
        a first mixture comprising:
            from about 1% to about 50% by weight of at least one starch;
            from about 1% to about 50% by weight of at least one liquid fatty substance; and
            from about 0.5% to about 40% by weight of at least one silica material;
            wherein the first mixture is a free-flowing powdered oil mixture; and
        a second mixture comprising:
            from about 1% to about 40% of at least one oxidizing agent;
            from about 0.5% to about 30% of at least one acrylic polymer; and
            from about 0.5% to about 10% of at least one chelant compound; and
    applying the resulting system to the hair,
    wherein the at least one oxidizing agent and at least one liquid fatty substance are present in a ratio ranging from about 0.48 to about 13.25,
    all weights above relative to the total weight of the hair color composition prior to mixing with a developer.

17. The method according to claim 16, comprising
mixing the at least one starch and at least one liquid fatty substance to create a white liquid mix; and
adding the at least one silica material to the white liquid mix.

18. The method according to claim 16, further comprising combining the first mixture and the second mixture to form the hair color composition prior to combining the hair color composition with the developer.

19. The method according to claim 16, further comprising leaving the composition on the hair for a time period of up to about 60 minutes.

20. A multi-compartment kit for altering the color of hair, comprising:
a first compartment comprising a first mixture comprising
from about 1% to about 50% by weight of at least one starch;
from about 1% to about 50% by weight of at least one liquid fatty substance; and
from about 0.5% to about 40% of at least one silica material;
wherein the first mixture is a free-flowing powdered oil mixture;
and
a second compartment comprising a second mixture comprising:
from about 1% to about 40% of at least one oxidizing agent;
from about 0.5% to about 30% of at least one acrylic polymer; and
from about 0.1% to about 10% of at least one chelant compound;
wherein the at least one oxidizing agent and at least one liquid fatty substance are present in a ratio ranging from about 0.48 to about 13.25,
all weights above relative to the total weight of the hair color composition prior to mixing with a developer.

21. A hair color-altering composition of claim 1 comprising:
a first mixture comprising:
from about 15% to about 25% of at least one starch chosen from corn starch;
from about 35% to about 40% of at least one liquid fatty substance chosen from mineral oil;
from about 10% to about 15% of at least one silica material chosen from sodium silicate, silicate silylate, and mixtures thereof; and
a second mixture comprising:
from about 15% to about 20% of at least one oxidizing agent chosen from potassium persulfate, sodium persulfate, and mixtures thereof;
from about 0.5% to about 1% of at least one acrylic polymer chosen from sodium polyacrylate;
from about 0.5% to about 2% of at least one chelant compound chosen from EDTA;
from about 1% to about 5% of at least one solid or semisolid wax chosen from PVP and polyethylene wax; and
from about 1% to about 10% of at least one surfactant chosen from sodium lauryl sulfate;
all weights above relative to the total weight of the hair color composition.

22. A hair color-altering composition of claim 21 comprising:
a first mixture comprising:
from about 20% to about 22% of corn starch;
about 40% of mineral oil;
about 13% of at least one silica material chosen from sodium silicate, silicate silylate, and mixtures thereof; and
a second mixture comprising:
from about 19% to about 20% of at least one oxidizing agent chosen from potassium persulfate, sodium persulfate, and mixtures thereof;
from about 0.5% to about 1% of at least one chelant compound chosen from EDTA;
from about 1% to about 2% of at least one solid or semisolid wax chosen from PVP and polyethylene wax; and
from about 1% to about 2% of at least one surfactant chosen from sodium lauryl sulfate;
all weights above relative to the total weight of the hair color composition.

* * * * *